United States Patent [19]
Blanz

[11] 3,951,527
[45] Apr. 20, 1976

[54] TARGET IMAGE PROJECTOR
[75] Inventor: John H. Blanz, Concord, Mass.
[73] Assignee: Narco Scientific Industries, Inc., Fort Washington, Pa.
[22] Filed: Sept. 12, 1974
[21] Appl. No.: 505,338

[52] U.S. Cl. .................................. 351/30; 351/23; 353/94; 353/98
[51] Int. Cl.² .................... A61B 3/02; G03B 21/26; G03B 21/28
[58] Field of Search ............ 351/23, 30, 31; 353/94, 353/98, 122

[56] References Cited
UNITED STATES PATENTS
3,235,321 2/1966 Jayle et al. ........................ 351/23 X
3,283,652 11/1966 Busch .............................. 353/94 X
3,827,789 8/1974 Molner et al. ..................... 351/30 X Primary Examiner—Paul A. Sacher
Attorney, Agent, or Firm—Wolf, Greenfield & Sacks

[57] ABSTRACT

An apparatus for measuring and evaluating a subject's visual field includes a projector for presenting a target image, consisting of a spot of light, at a series of selected locations within the subject's visual field. A mirror is mounted for movement about a pair of axes and is rotated to a desired attitude by step motors which control the position of the mirror about the respective axes. A light beam is directed toward the mirror and is reflected in a direction dependent on the attitude of the mirror as controlled by the step motors.

5 Claims, 7 Drawing Figures

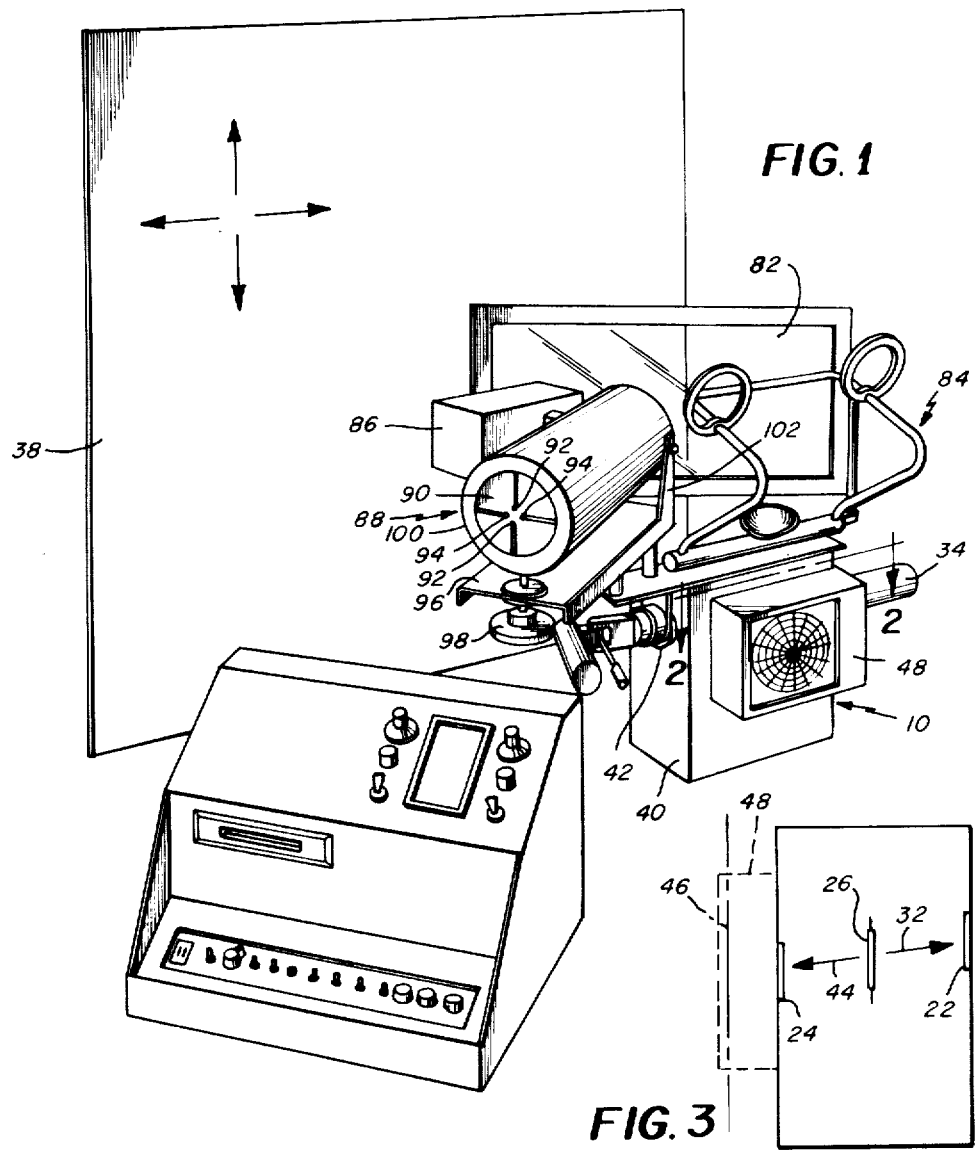
FIG. 1
FIG. 3
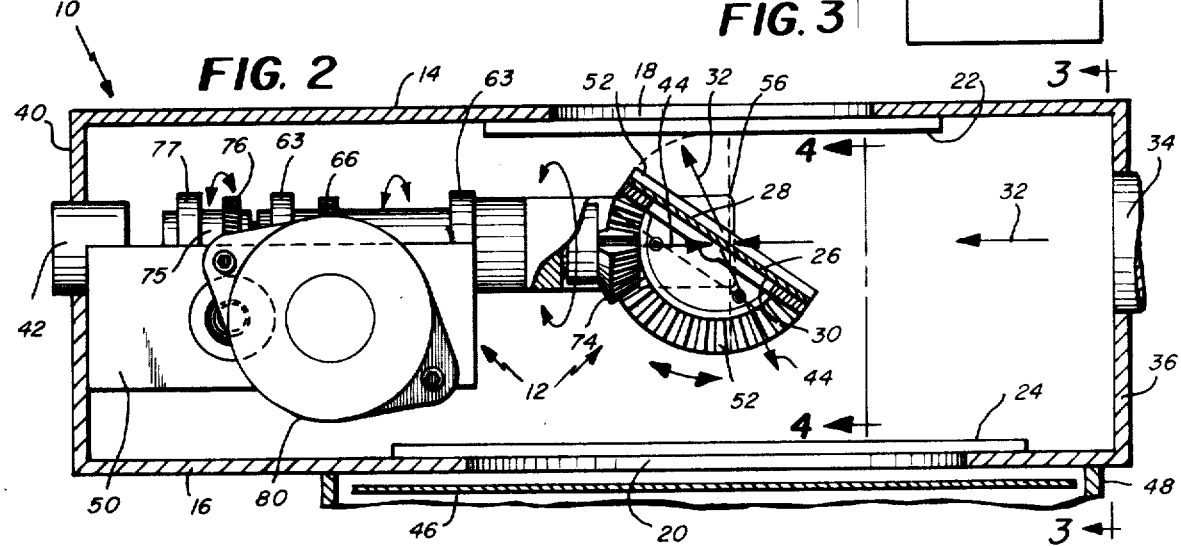
FIG. 2

TARGET IMAGE PROJECTOR

BACKGROUND OF THE INVENTION

This invention relates to a target projector such as might be used, for example, in automatically testing one's visual field. Measurement of one's visual field is important for a variety of reasons including the diagnosis of glaucoma as well as other human visual system diseases or impairments. In general, the prior techniques for determining one's visual field and any blind spots have been quite slow and tedious and require a definite subjective response from the person being tested in order to determine whether he has sighted the target at a particular location in his visual field. Additionally, the previously employed tests require administration by one having relatively high degree of skill such as an ophthalmic technician, optometrist or ophthalmologist. For example, in the most common type of visual field test, a hand-held target such as a small disc at the end of a wand, is moved about the subject's visual field by the examiner while the subject fixates on a central point. During movement of the hand-held target through the subject's field, the examiner asks the subject repeatedly whether he can see the movable target as it is passing from location to location. The examiner may plot, manually, the location of each point which is seen by the subject, or alternatively, he may plot those locations which the subject is unable to see, and which, therefore, define his blind spot.

In order to overcome the uncertainties and difficulties in the foregoing prior testing techniques improved techniques have been developed to automate the foregoing visual field test and to obtain an objective evaluation of the subject's visual field. By way of example, an improved method and apparatus is described in U.S. Pat. application Ser. No. 286,422, filed Sept. 15, 1972. The technique includes a means for projecting, automatically, and in sequence, a plurality of target images to the subject in selected, various locations within his visual field.

SUMMARY OF THE INVENTION

My invention relates to an improved target image projector usable, for example, in a system of the type described above. The target image projector includes a projection light source which develops a narrow collimated light beam. The position of the light beam and target image on the screen is determined by reflecting the beam, from its source, off one surface of a double faced mirror toward the screen. The attitude of the mirror is controllable to selectively direct the beam in the desired direction by stepping motors which may be positioned in accordance with preprogrammed digital information. The location of the target image on the screen, as presented to the subject, may be recorded permanently and automatically on photographic film incorporated into the projector. The photographic recording is made by employing a second light beam which is reflected off the opposite face of the controlled mirror toward the photograph film. The second, reflected beam is directed along the same axis as the first projection beam, but from the opposite direction and impinges on the film at a location which is dependent on the angle of incidence of the beam to the mirror which corresponds to the direction of the light beam which impinges on the target screen. Shutters are provided in association with each of the first and second light beams, the first shutter being employed to control the timing and duration of presentation of the target light and the second shutter means being employed to expose the photographic film to the second beam.

The mirror is mounted for rotational movement about each of a pair of perpendicular axes and one stepping motor is associated with each of the axes to rotate the mirror in incremental steps about its respective axes.

It is among the primary objects of the invention to provide an improved target image projector.

Also among the objects of the invention is to provide a light beam projector which is readily usable in a system for presenting target images at predetermined locations in accordance with preprogrammed digital information.

A further object of the invention is to provide a projector of the type described which is of simple construction and is compact.

DESCRIPTION OF THE DRAWINGS

The foregoing and other objects and advantages of the invention will be understood more fully from the following further description thereof, with reference to the accompanying drawings wherein:

FIG. 1 is an illustration of a system in which the invention may be employed;

FIG. 2 is a sectional plan illustration of the mirror positioning mechanism as seen from line 2—2 of FIG. 1 and showing portions of the mechanism broken away;

FIG. 3 is a diagrammatic sectional elevation as seen along the line 3—3 of FIG. 2;

DESCRIPTION OF THE PREFERRED EMBODIMENT

Figure 4:
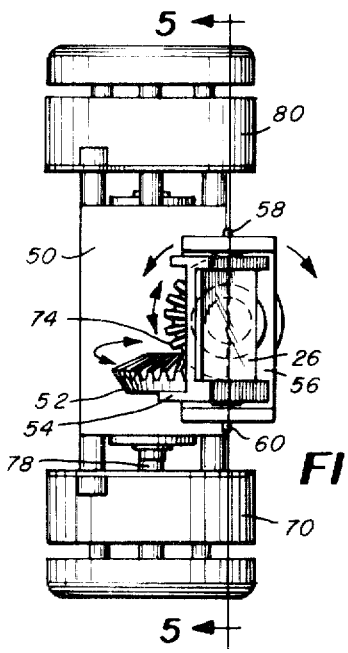
FIG. 4 is a side elevation of the mirror positioning mechanism as seen along the line 4—4 of FIG. 2.
Figure 6:
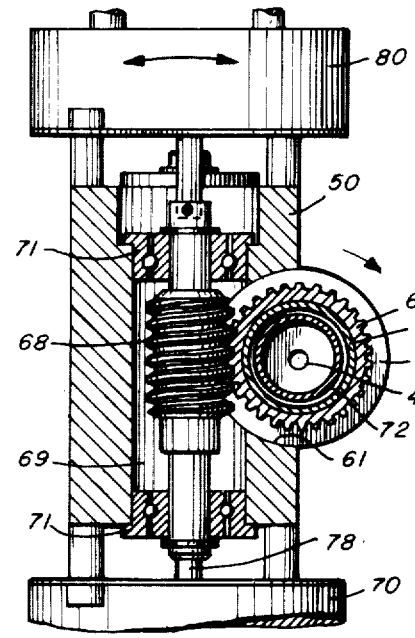
FIG. 6 is a sectional elevation of the mirror positioning mechanism as seen along the line 6—6 of FIG. 5.
Figure 5:
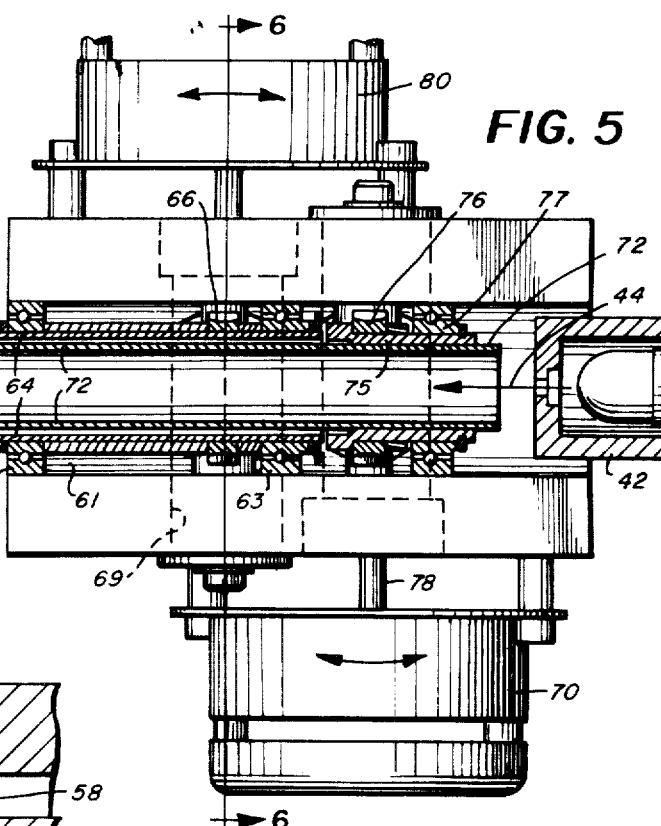
FIG. 5 is a sectional view of the mirror positioning mechanism as seen along the line 5—5 of FIG. 4.
Figure 7:
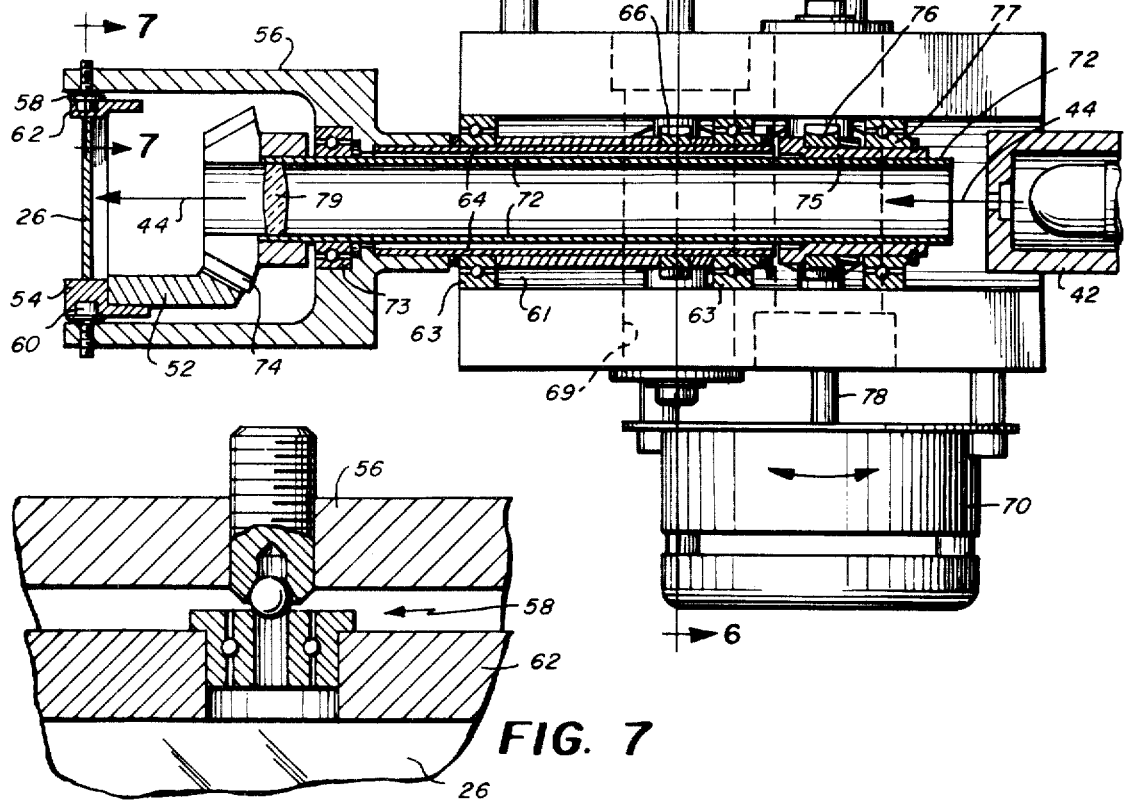
FIG. 7 is an enlarged illustration of the low friction bearing by which the mirror is mounted.

FIGS. 1–3 shows generally a visual fields testing system including a projector-camera housing 10 in which is mounted the mirror mechanism 12. The housing 10 includes a front wall 14 and a rear wall 16, having apertures 18, 20 respectively which can be opened or closed by a projection shutter indicated diagrammatically at 22 and film shutter indicated diagrammatically at 24. The mirror mechanism 12 includes a double faced mirror 26 having a front face 28 and a rear face 30. The mirror 26 is arranged so that it will reflect a collimated light beam 32 from a projection light 34, mounted to a sidewall 36 of the housing 10 through the projection shutter 22 and onto the projection screen 38. The opposite sidewall 40 of the housing 10 supports a second light source 42 which directs a beam of light 44 toward the rear face 30 of the mirror 26 along the same axis as that of the light beam from the projection light 34. The beam from the recording light source 42 is reflected from the mirror surface 30 in a direction which is opposite that of the reflected projection beam 32 from the front face 28 of the mirror 26. The recording light beam 44 is directed toward a film plane, indicated diagrammatically at 46 and disposed at the rear of the housing 10 by any of a variety of well-known film holding devices 48. The double faced mirror 26 thus directs the projection beam 32 to a selected location on the screen and simultaneously directs the recording beam 44 to a corresponding location in the film plane 46, depending on the attitude of the mirror 26.

The mirror 26 is mounted for adjustable movement by the mirror mechanism 12 in which the mirror 26 is rotatable about each of a pair of perpendicular axes. The mirror mechanism includes a support block 50 which is secured to the interior of the housing 10. The mirror mechanism 12 includes a driven bevel gear segment 52. The mirror 26 is secured with respect to and across the diameter of gear 52 by a bracket 54 and lies in a plane perpendicular to that of the gear 52 and which coincides with the axis of rotation of the gear 52. The mirror 26 and gear 52 are supported for rotation in unison about the rotational axis of the gear 52 by means of a yoke 56 having low friction bearings 58, 60 which support the upper edge of the mirror, by bracket 62, and the opposite face of the gear 52, by bracket 54, to enable the mirror 26 and gear 52 to rotate in unison about the common axis defined by the bearings 58, 60.

The yoke 56 is mounted for rotation about a horizontal axis perpendicular to the axis defined by bearings 58, 60 to rotate the mirror 26 and gear 52 bodily about that horizontal axis. To this end the yoke 56 is secured to the end of an outer cylinder 64 which is rotatably mounted within a cylindrical cut-out 61 formed along one side of the block 50 as by ball bearings 63 which are securely mounted to the cut-out 61. The cylinder 64 has a worm gear 66 secured thereto which is driven by a worm 68 which is driven, in turn, by a stepping motor 80 mounted to the block 50. The worm 68 is disposed within a bore 69 formed in the block 50 and may be supported by bearings 71. The mirror 26 and gear 52 are driven with respect to the yoke 56 by means of an inner cylinder 72 which extends through the outer cylinder 64. An end of the inner cylinder 72 extends into and is journaled to the yoke at bearing 73. The other end of the inner cylinder 72 extends rearwardly beyond the end of the outer cylinder 64. The rear, protruding end of cylinder 72 has a collar 75 secured thereto and the collar 75 is rotatably mounted within cut-out 61 of the block 50 by bearing 77. A bevel gear 74 is secured to the end of the inner cylinder 72 which projects into the yoke 56 and meshes with the driven beveled gear 52 to which the mirror is mounted. The inner cylinder 72 is rotated by means of a worm gear 76 secured to the collar 75. Gear 76 is driven by a worm connected to the drive shaft 78 of stepping motor 70 in the same manner as described above with regard to worm 68. The stepping motors 70, 80 are operated in response to appropriate electrical signals from the controlling electronic circuitry to pulse the motors incrementally to their intended positions. The motors 70, 80 may be selected from a wide variety of commercially available devices and preferably are reversible.

The recording light 42 is mounted in the housing and extends into the rearward end of the cut-off 61 in the block in alignment with the axis of rotation of the cylinders 64, 72. The recording light thus passes axially through the hollow inner cylinder 72 and, if desired, suitable lenses, such as suggested at 79 may be mounted within the hollow inner cylinder 72 to maintain the light beam collimated. The projection light source 34 is mounted to the opposite side wall of the housing, also in substantial alignment with the axis of rotation of the cylinders so that both light beams will be directed substantially along the same horizontal axis and will be reflected in substantially opposite directions.

It may be noted that the axis of rotation of the mirror defined by the bearing 58, 60 is a movable axis in that it intersects, perpendicularly, and is rotatably about the horizontal axis of the cylinders 64, 72. It may be noted further that operation of one of the step motors 70, 80 usually will result in movement of the mirror in a compound direction, e.g., rotation of the yoke alone usually will also cause some rotation of the mirror about the axis defined by its bearings 58, 60. When such compound motion is not desired, it may be corrected by operating the other of the stepper motors in a reverse direction to compensate and drive the inner cylinder to return the mirror to its desired position about the movable axes. This may be accomplished by suitable electronic control of the stepping motors 70, 80 and reference is made to an application of Marvin E. Jernigan filed of even date herewith for a description of one such control system. Similarly, the operation of the projection and recording lights as well as the projection and recording shutters may be controlled electronically as described in said application.

The invention is illustrated as being employed in connection with a visual fields testing system which may also include a partially reflective plate 82 mounted above and forwardly of the housing 10 so as to be directly in front of the subject's view when his head is properly placed in the head rest and chin support 84. Plate 82 is adapted to enable the subject to view the screen 38 and is disposed at an angle to his general line of sight to enable a light source 86, preferably infrared, to reflect from the plate 82 and illuminate the subject's eyes. The image from the subject's eyes is, in turn, reflected from the plate 82 toward an imaging arrangement 88 which includes a ground glass screen 90 on which the reflected image of the subject's eye may be focused, employing the technique described in the aforementioned U.S. patent. As described in that patent a pair of vertically spaced photoelectric cells 92 and horizontally spaced photoelectric cells 94 are located on or adjacent the screen 90 and are aligned with selected regions of the image of the subject's eye on the screen 90. Variations in the output signals from the photocells 92, 94 are dependent on the direction and magnitude of the subject's eye movements and their signals may be electronically processed. Imaging arrangement 88 preferably is mounted for adjustment to the housing 10 to facilitate initial alignment of the photocells 92, 94 with the subject's eye image on the screen 90. This may include a bracket 96 pivoted for horizontal movement to the housing 10 and a vertical elevation screw 98 carried by the bracket 96 and in engagement with the end of the barrel 100, the other end of the barrel 100 being pivoted to the bracket at trunnions 102.

While the invention has been described primarily for use in a visual fields testing system, it may be employed in other environments where it is desirable to control the direction of a beam of light. It should be understood that the foregoing description of the invention is intended merely to be illustrative thereof and that other modifications and embodiments may be apparent to those skilled in the art without departing from its spirit.

Having thus described the invention what I desire to claim and secure by Letters Patent is:

1. An apparatus for projecting a target image to a selected variable location comprising:
   a light source;
   a double faced mirror mounted in relation to said light source to reflect a light beam from said source off one surface of the mirror;
   means mounting said mirror for rotational movement about at least two intersecting, perpendicular axes;
   first drive means operatively associated with said mirror for rotating said mirror about one of said axes;
   second drive means operatively associated with said mirror for effecting rotation of said mirror about the other of said axes, said first and second drive means being operable independently of each other;
   said mirror mounting means being constructed and arranged so that one of said axes will rotate in unison with said mirror and about said other axis when said mirror is rotated about said other axis;
   said light source being mounted along said other axis and being constructed and arranged to direct the light emitted therefrom substantially along said other axis toward said mirror;
   a second light source mounted with respect to said mirror and said other axis to direct the light emitted therefrom toward the opposite surface of said mirror and along said other axis whereby the light from said first and second light sources may be reflected from said mirror in opposite directions.

2. An apparatus for projecting a target image to a selected variable location comprising:
   an outer cylindrical member and an inner cylindrical member disposed concentrically within said outer cylindrical member;
   said cylindrical members each being rotatable about their common axis independently of and with respect to each other;
   a mirror supported by one of said cylindrical members for rotation in unison therewith about said axis, said mirror further being mounted to said one of said cylindrical members for rotation about a second axis which intersects and is perpendicular to said common axis;
   means connecting the other of said cylinders to said mirror for rotating said mirror about the second axis in response to rotation of said other of said cylinders;
   a light source mounted to direct the light therefrom along said first axis and through the inner of said cylinders toward said mirror;
   first drive means connected to said one cylinder for rotating said mirror about said common axis; and
   second drive means connected to the other of said cylinders for effecting rotation of the mirror about the second axis, said first and second drive means being operable independently of each other.

3. A device as defined in claim 2 wherein said mirror mounting means further comprises:
   a yoke mounted to said one of said cylindrical members for rotation in unison therewith about said one axes;
   means mounting said mirror for rotation to said yoke and about said other axis, said other axis intersecting said one axis and being perpendicular thereto;
   gear means connecting said mirror to the other of said cylindrical members for rotation of said mirror within said yoke in response to rotation of said other of said cylinders.

4. A device as defined in claim 3 wherein said first and second drive means each comprises:
   a step motor; and
   gear means connecting each of said step motors to its associated cylindrical member.

5. A device as defined in claim 2 further comprising:
   said inner cylindrical member being longer than the outer cylindrical member, the inner cylindrical member having a rear end which protrudes rearwardly beyond the rear end of the outer cylindrical member;
   said second drive means being connected with the rearwardly protruding end of said inner cylindrical member.

* * * * *